United States Patent [19]

Ohayon et al.

[11] Patent Number: 4,712,562
[45] Date of Patent: Dec. 15, 1987

[54] OUTPATIENT MONITORING SYSTEMS

[75] Inventors: Jacques J. Ohayon, 316 Oakville Dr., Pittsburgh, Pa. 15220; Glen P. Williams, Pittsburgh, Pa.

[73] Assignee: Jacques J. Ohayon, Pittsburgh, Pa.

[21] Appl. No.: 914,088

[22] Filed: Oct. 1, 1986

Related U.S. Application Data

[63] Continuation of Ser. No. 689,655, Jan. 8, 1985, abandoned.

[51] Int. Cl.⁴ ............................................... A61B 5/02
[52] U.S. Cl. ..................................... 128/672; 128/695
[58] Field of Search ............... 128/670, 672, 695–697, 128/700, 706, 709–710, 904

[56] References Cited

U.S. PATENT DOCUMENTS

| Re. 31,247 | 5/1983 | Johnstone | 364/474 |
|---|---|---|---|
| 3,724,455 | 4/1973 | Unger | 128/706 |
| 3,819,863 | 1/1974 | Slaght | 178/904 |
| 3,920,005 | 11/1975 | Gombrich et al. | 128/904 |
| 4,068,096 | 1/1978 | Rattenborg et al. | 128/904 |
| 4,068,097 | 1/1978 | Verriest | 179/2 A |
| 4,159,018 | 6/1979 | Brastad | 128/697 |
| 4,173,971 | 11/1979 | Karz | 128/702 |
| 4,252,127 | 2/1981 | Gemelke | 128/680 |
| 4,319,241 | 3/1982 | Mount | 340/879.38 |
| 4,337,778 | 7/1982 | Akira et al. | 128/680 |
| 4,458,693 | 7/1984 | Badzinski et al. | 128/715 |

OTHER PUBLICATIONS

Laughlin et al., "Blood Pressure During Self-Recording of Home Blood Pressure" American Heart Journal, 98(5):629–634 (1978).

Gould et al., "Assessment of the Accuracy and Role of Self-Recorded Blood Pressures in the Management of Hypertension" British Medical Journal, 285:1691–1694 (1982).

Cottier et al., "Usefulness of Home BP Determination in Treating Borderline Hypertension" JAMA, 248(5):555–558 (1982).

Haynes, "Improvement of Medication Compliance in Uncontrolled Hypertension", The Lancet, Jun. 12, 1976, pp. 1265–1268.

Wingerson, "Hypertension Compliance" Medical World News, May 30, 1977, pp. 20–29.

Burch, "Signed Opinion" Hypertension, 1(1):32 (1975).

Primary Examiner—William E. Kamm

[57] ABSTRACT

The invention provides a system and a method for obtaining from the patient's body information pertaining to the blood pressure and heart rate of a patient for the purpose of enabling a physician to monitor and prescribe treatment intended to maintain a patient's blood pressure within a predetermined range, for encouraging the patient to follow the treatment and for collecting information relating to the patient's blood pressure and heart rate. Signals are generated that represent the level of blood pressure and pulse rate of a patient in a form suitable for telephonic communication. The signals are transmitted to a remote central digital processor for storage and analysis. Data resulting from the analysis is submitted to the patient or physician. An off hook and ring detect circuit is provided preventing actuation of the system when telephonic access is unavailable.

3 Claims, 9 Drawing Figures

TELEMANOMETER CIRCUIT BLOCK DIAGRAM

MODEM and SPHYG INTERFACE FIG. 6

FIG. 7

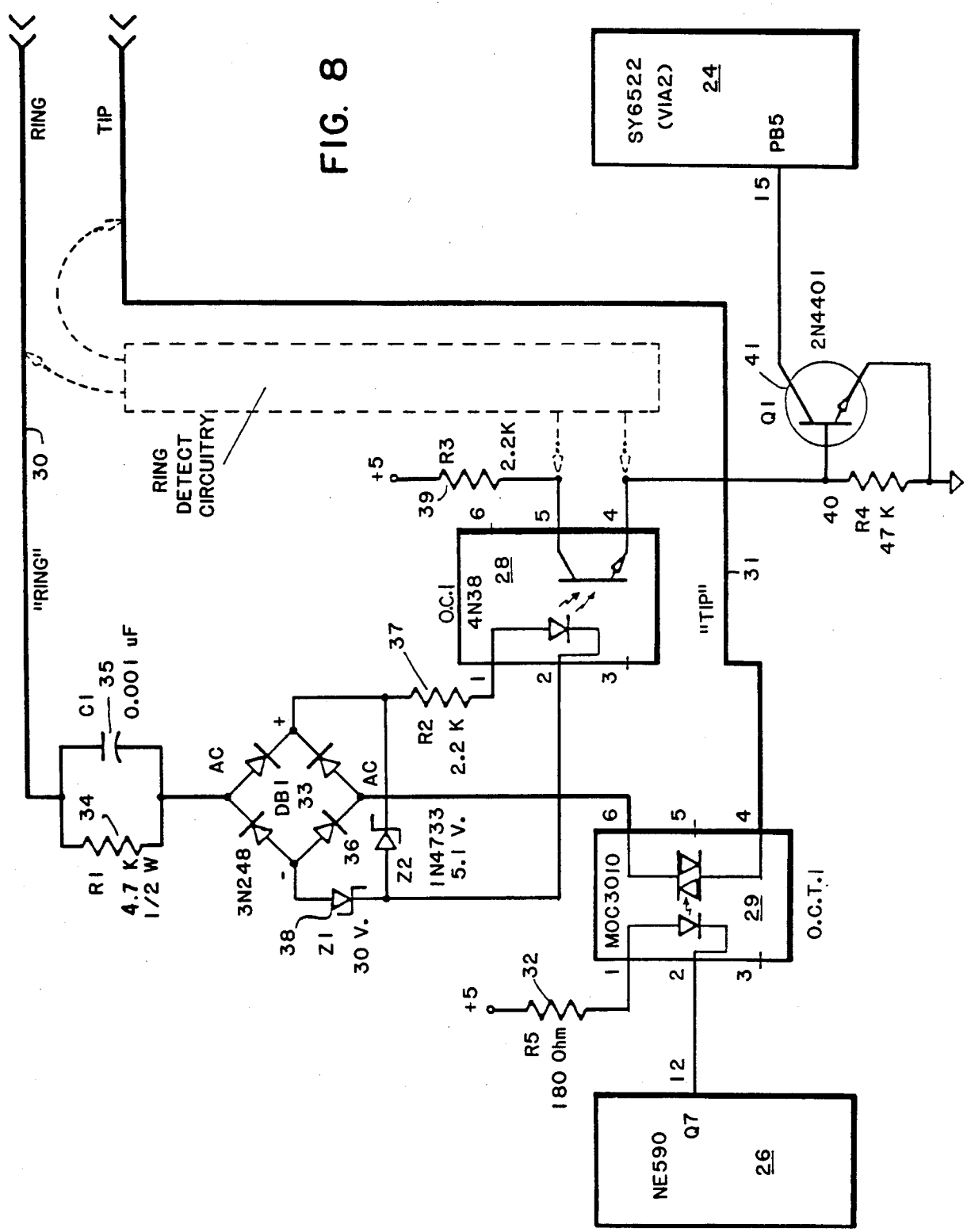

OUTPATIENT MONITORING SYSTEMS

This is a continuation, of application Ser. No. 06/689,655, filed Jan. 8, 1985, now abandoned.

FIELD OF THE INVENTION

The invention relates to the continuous treatment and diagnosis of blood pressure disorders as well as the monitoring of a prescribed treatment of medication for a patient on an ongoing basis.

DESCRIPTION OF THE PRIOR ART

It has been a long standing goal in the heath care community to integrate advanced communications systems with information processing systems to provide superior medical services. By way of example, U.S. Pat. No. 4,004,577 discloses a method for treating coronary prone patients when heart attack symptoms occur before qualified direct contact personal care can be administered to the patient. A device provides auditory signals indicative of the existing heart beat condition and telephone communication is established between the patient and a source capable of making a qualified response based on the auditory signals.

There has been a continuing need for improved monitoring techniques for patients suffering from blood pressure disorders, such as hypertension or hypotension. Hypertension, in particular is a prevalent health problem in the United States and is the major cause of early death and serious disability in an estimated 25 million persons annually. One of the most menacing aspects of hypertension is the fact that it remains undetected and untreated in many persons and, therefore, causes permanent damage before it can be discovered. Since blood pressure normally varies in healthy persons, the state of hypertension is influence blood pressure, the measurement of a single elevated blood pressure is not necessarily significant. However, every person with a blood pressure reading above normal should be reexamined several times to determine if the measurement persists. The treatment of a blood pressure disorder is subject to the same difficulty as the initial detection of that disorder, that is, the many factors which influence blood pressure.

Therefore, there is a need for a method for obtaining information pertaining to the blood pressure and heart rate of a patient in an outpatient environment and for providing an analysis of that information. Further, there is a need for a method for enabling a physician to prescribe treatment intended to maintain a patient's blood pressure within a predetermined range and for collecting information relating to the patient's blood pressure. There also exists a need for a method for enabling a physician to prescribe treatment intended to maintain a patient's blood pressure within a predetermined range for encouraging the patient to follow the treatment and for collecting information relating to the patient's blood pressure by periodically generating and storing such information for selective later anaylsis.

SUMMARY OF THE INVENTION

The invention is a system and method, each of which provides information pertaining to the blood pressure and heart rate of an outpatient. The information enables a physician to monitor and prescribe treatment and can be utilized to encourage the patient to follow a prescribed course of treatment by the scheduled monitoring of his own condition. The invention. includes a method and system for generating a first signal representative of the patient's vital signs and a second signal identifying the individual patient from one or more other patients monitored using the present method. The signals are in a form suitable for telephone communication with a central digital processor which analyzes and stores the information. The information is then submitted to the patient or the patient's physician. The physician can use the information, at least in part, in reaching a prescribed course of treatment for his patient.

BRIEF DESCRIPTION OF THE DRAWINGS

The above as well as other features and advantages of the present invention will be more clearly appreciated through a consideration of the detailed description of the invention in conjunction with the drawings in which

FIG. 7 is a schematic diagram of lights and switches in the preferred system of FIG. 3; and FIG. 8 is a schematic diagram of the off-hook and ring detect circuit of this invention.

DETAILED DESCRIPTION OF THE PREFERRED EMBODIMENTS

Figure 1:
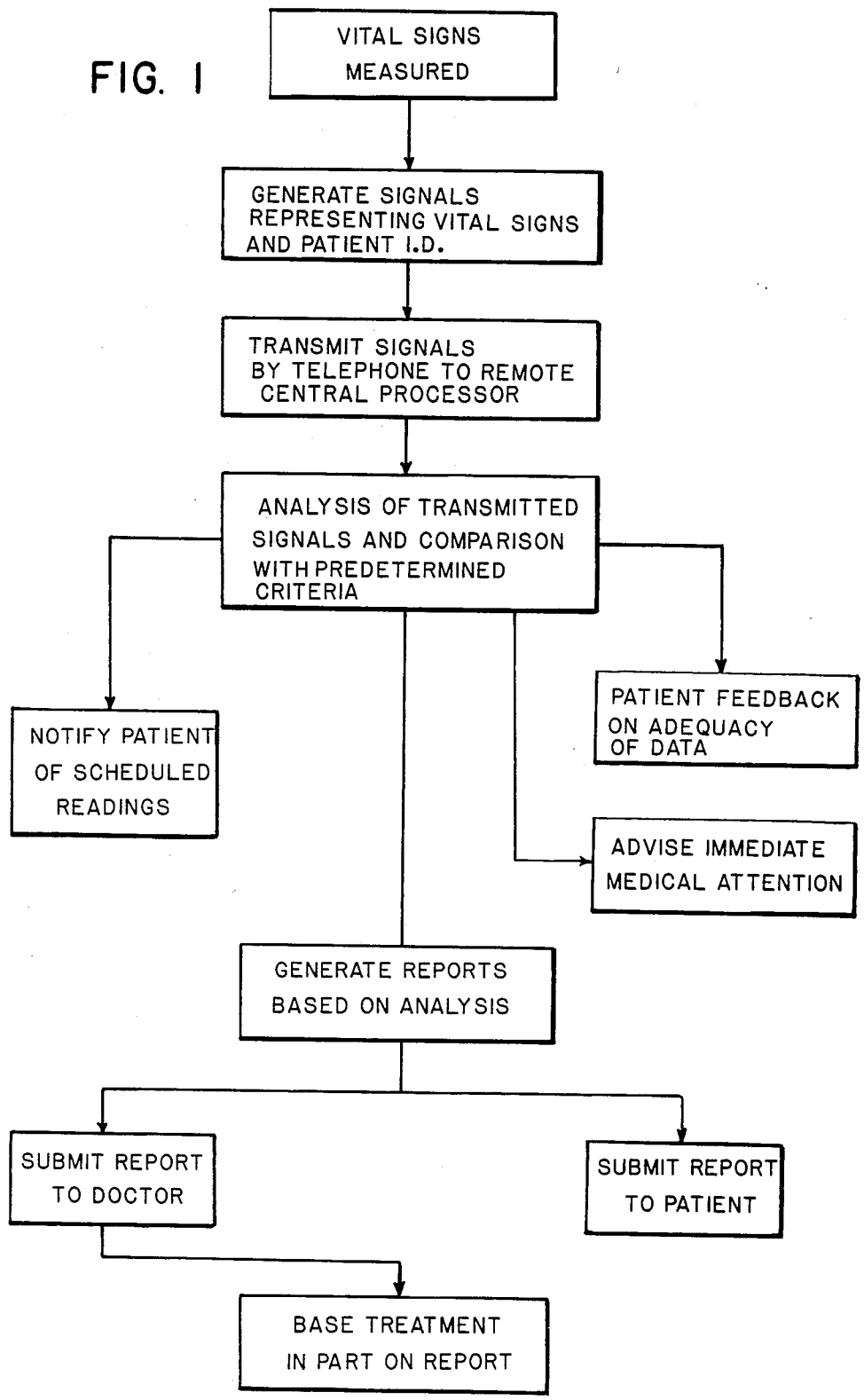
FIG. 1 is a block diagrammatic representation of the method of the invention.

The present invention provides a method and system through which several objectives can be accomplished. Patient compliance with a prescribed course of medical treatment as well as the effectiveness of the treatment can be monitored, recorded and analyzed. The patient's medical condition can be periodically monitored over an extended period of time on an outpatieht basis in order to provide the treating physician with an additional diagnostic tool. The patient can also be provided with a treatment feedback system which enables the patient to recognize his compliance with, or his failure to adhere to, a particular course of medical treatment. Such a feedback system also facilitates an analysis of the patient's developing medical history and a comparison of the patient's condition with the original prognosis coupled to a predetermined course of treatment.

It is to be appreciated that a variety of individual pieces of equipment can be integrated into the system of the present invention which carries out the method of this invention. The equipment itself is available and upon a full appreciation of the invention, those skilled in the art will recognize that substitutions to the equipment so utilized can be made and that such substitutions are well within the scope of the invention as defined by the several claims appended hereto.

Accordingly, the following description of equipment employed by the system is provided only as an example. The present trend in the production of instrumentation for use in blood pressure and heart rate measurement is toward the manufacture of automatic or semi-automatic devices. The present invention contemplates the use of an electronic sphygmanometer in which a microphone or transducer is provided for the detection of korotkoff sounds. A microprocessor can be included to control inflation and deflation rates of the cuff on the patient's arm. The information obtained from the transducer is converted into a signal suitable for telephone transmission by means of a system as typified in U.S. Pat. No. 4,068,096, the contents of which are incorporated herein by reference. Another example of a suitable communication system for use with existing telephone equipment is commercially available and consists of a pair of send/receive acoustic coupling systems or modems. It is anticipated that the several individual components described above could be incorporated into a single integrated apparatus comprising an electronic sphygmanometer with automatic telephone dialing and modem capabilities which permits a very large number of individual patients to transmit vital blood pressure and heart beat functions to a central computer facility. The central facility would include equipment for establishing two way communication with a patient to provide both instantaneous feedback as well as later hard copy information, such as a print out of the patient- 'medical status and a record of the blood pressure and heart beat information submitted to the central facility.

FIG. 1 describes the several steps of the present invention followed by the system of the present invention. The method provides information pertaining to the blood pressure and heart rate of an identifiable patient and is presented in FIG. 1 in block diagrammatic form. The method permits the monitoring of the blood pressure and heart rate of at least one patient in a group of patients, the number of which is limited only by the capability of a remote central data collecting and processing system. Each patient is provided with a device which the patient can employ to take his own heart rate and blood pressure. The device includes apparatus which generates a signal representing the blood pressure, that is a systolic value and a diastolic value, and heart rate of the patient. The device also includes apparatus which generates a second signal which represents the identity of the patient. Such a signal could provide, for example, the patient's name, social security number or some such similar coded indicia which particularly identifies a specific patient within the monitoring network. The patient identification signal is preferably provided through the programming of an electrically alterable memory device. Thus, a particular device is adaptable to the indicia requirements of the health care system which is utilizing the method of this invention. Both signals representing the patient's monitored vital signs and the patient's identity are generated in a format which is suitable for telephonic transmission.

The patient's blood pressure, heart rate and identity signals are then transmitted, over telephone lines, to a remote central data collecting and processing system which stores the monitored vital sign signals in a patient file in a form suitable for later access. The signals are analyzed by the processing system and compared to a set of predetermined criteria established by the patient's treating physician. The results of the analysis are then submitted to the patient. As a result, the patient gains the advantage of regular feedback concerning his blood pressure.

The results of the blood pressure data analysis can be supplied to the patient's physician. Based at least in part on the analysis results, there can also be submitted to the patient information specified by his physician pertaining to his measured and analyzed blood pressure and heart rate.

While the collection analysis and feedback of medical information has been described in conjunction with a single patient and that patient's physician, it is to be understood that, by employing the aforedescribed indicia system, more than one physician can be provided with information pertaining to a single patient and that more than one physician can be in communication through this method with the data reflecting the immediate condition of the physician's respective patients.

The method also includes steps by which immediate feedback to the patient can be effected. Upon receipt of the signals representing the patient's blood pressure, the central data collecting and processing system can make an immediate determination as to whether or not the incoming data is sufficient for analysis, and activate an indicia means, such as a warning light, at the patient's location advising the patient that an additional blood pressure reading is required for analysis. Also, if the reading is abnormal for a particular patient, the central data collecting and processing system can be programmed to request that the patient take one or more additional readings, or signal the patient or the patient's physician that immediate medical attention is advisable.

Under what could be described as a typical patient monitoring and information feedback program, the patient's blood pressure information and analysis would be generated in a hard copy format for distribution to the patient and his physician. Additionally, notices could be periodically generated, if necessary, to remind the patient of the required schedule for vital signs readings.

While specific medications are readily available for the treatment of blood pressure related disorders, the particular dosage which is suitable to the unique condition of a particular patient must be carefully monitored and controlled. According to the techniques of this invention, the presumptive aspect of dosage determination can be substantially eliminated through the continuous monitoring and analysis of the patient's condition. The method represented by the block diagram enables a physician to prescribe treatment intended to maintain a patient's blood pressure within a predetermined range to both encourage the patient to follow the treatment through continuous monitoring and the behavioral reinforcement of frequent feedback, and to collect information relating to the patient's blood pressure to establish a complete history of the treatment process.

Figure 2:
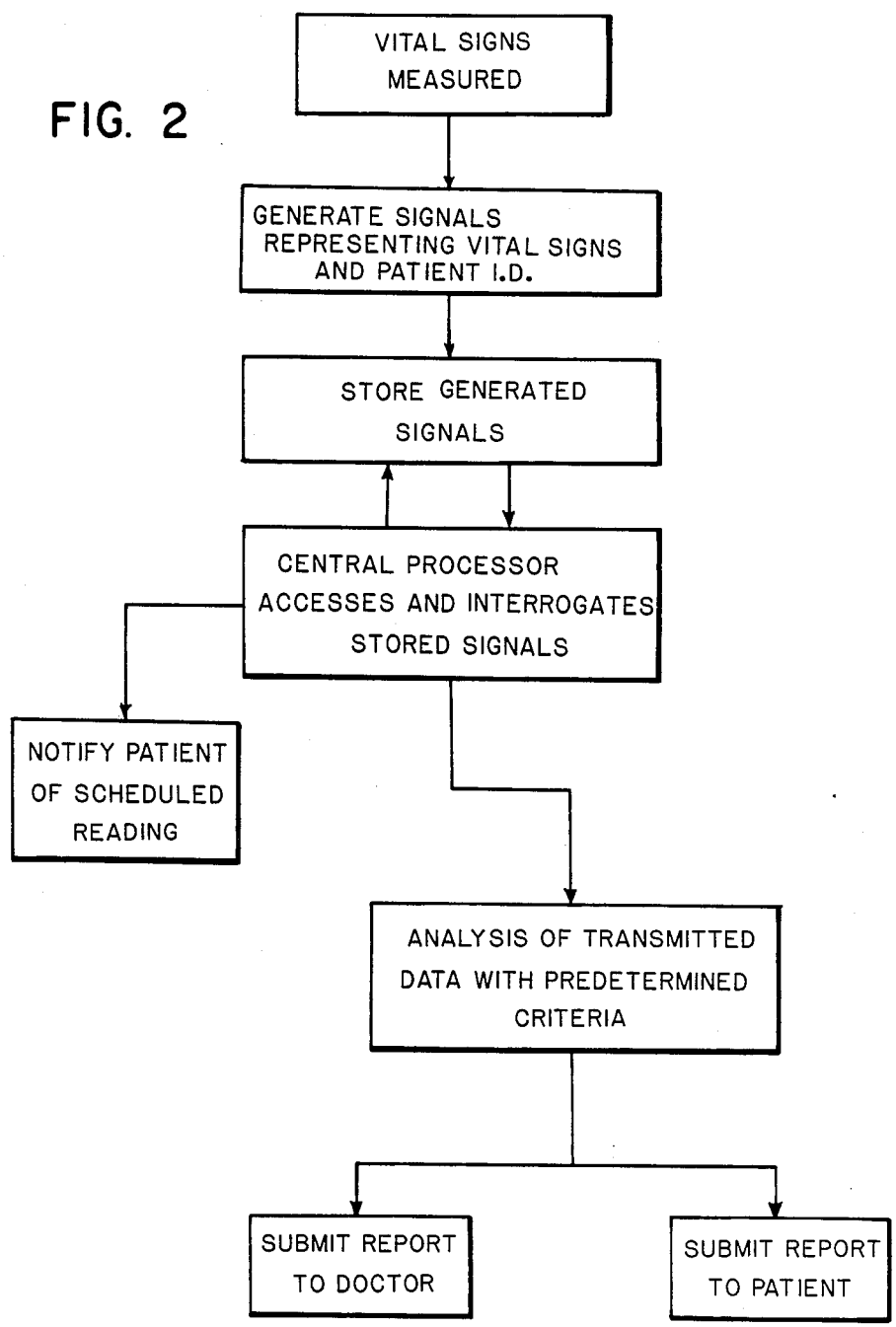
FIG. 2 is a block diagrammatic representation of an alternative embodiment of the method of the invention.
Figures 1, 3:
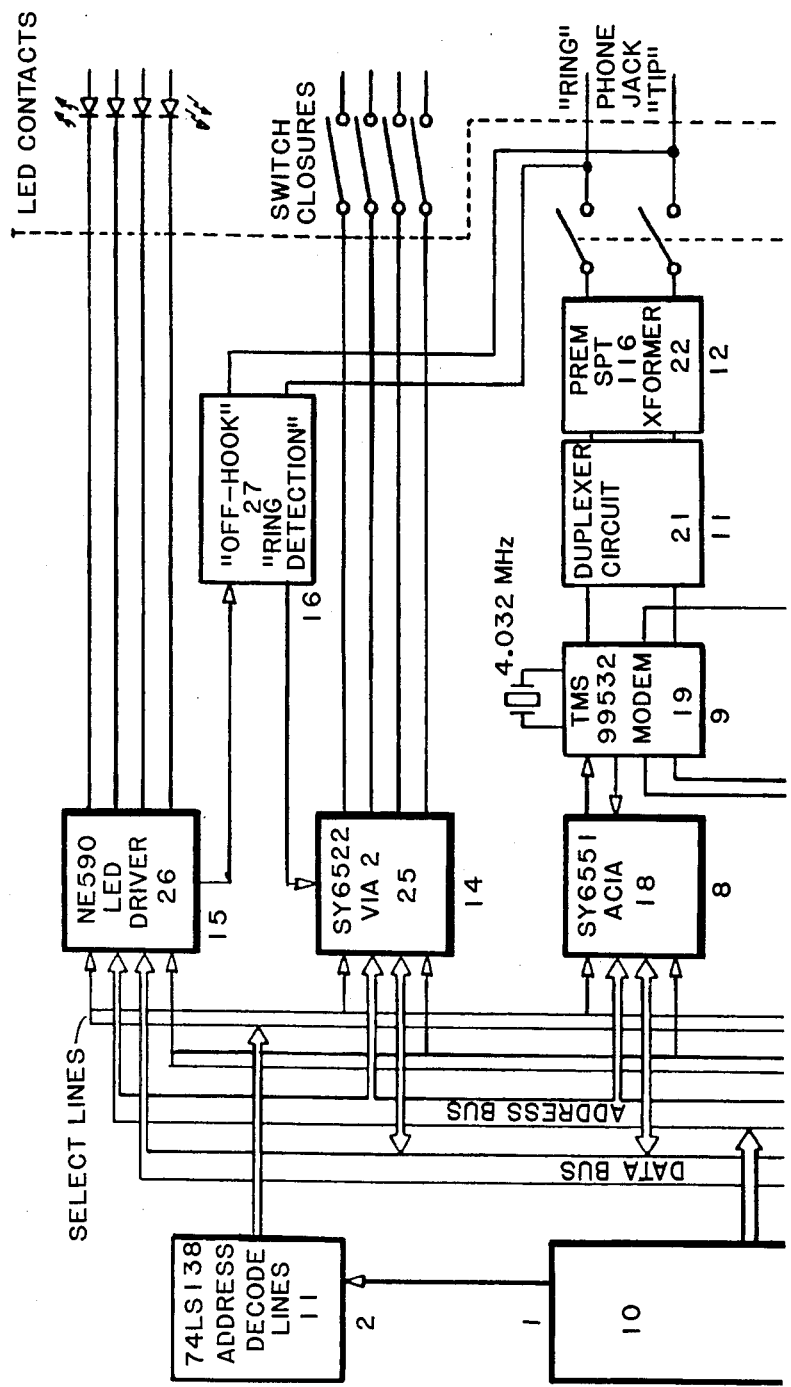
FIG. 3 is a telemanometer block diagram for a preferred embodiment.
Figures 2, 3:
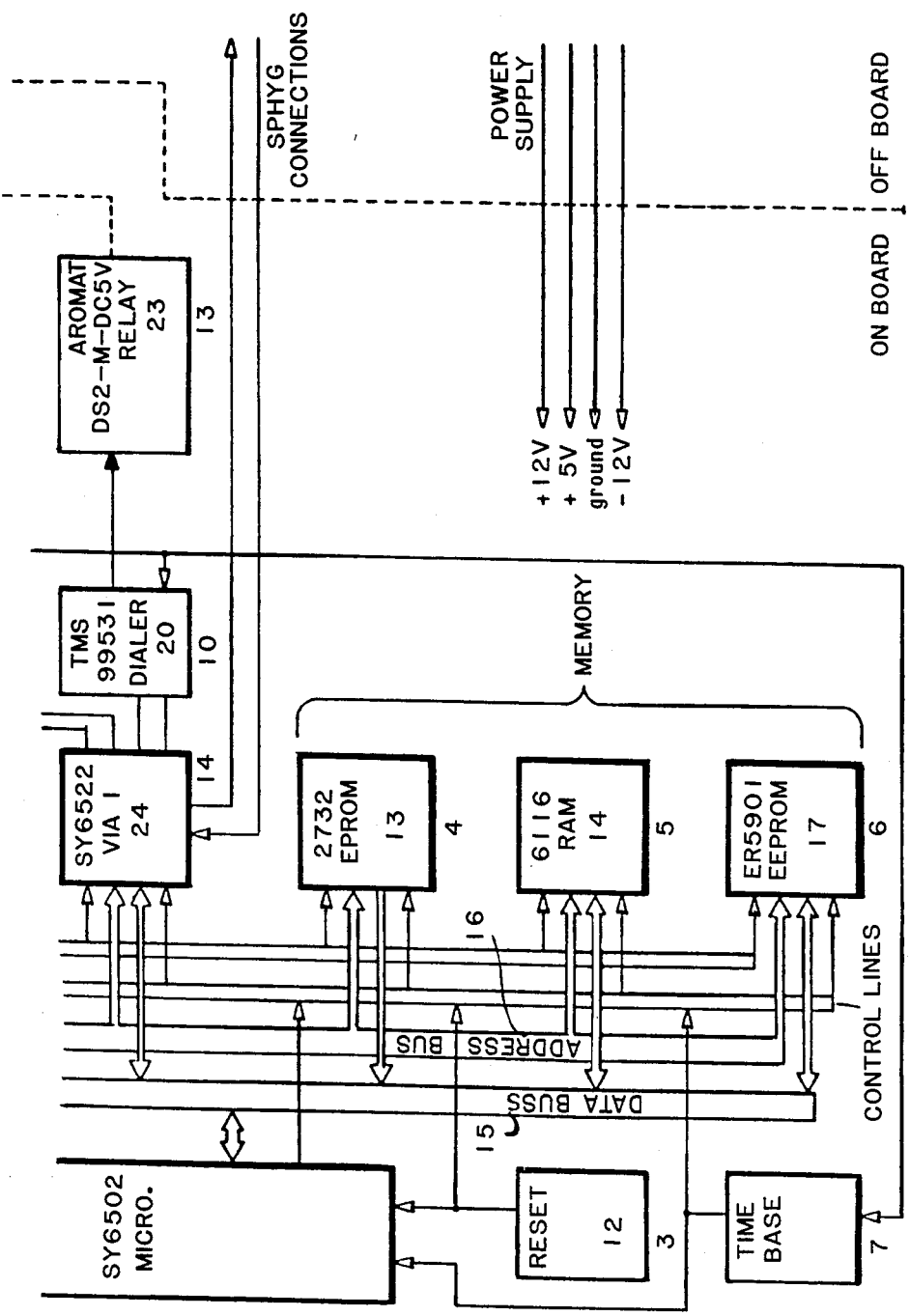
Figure 4:
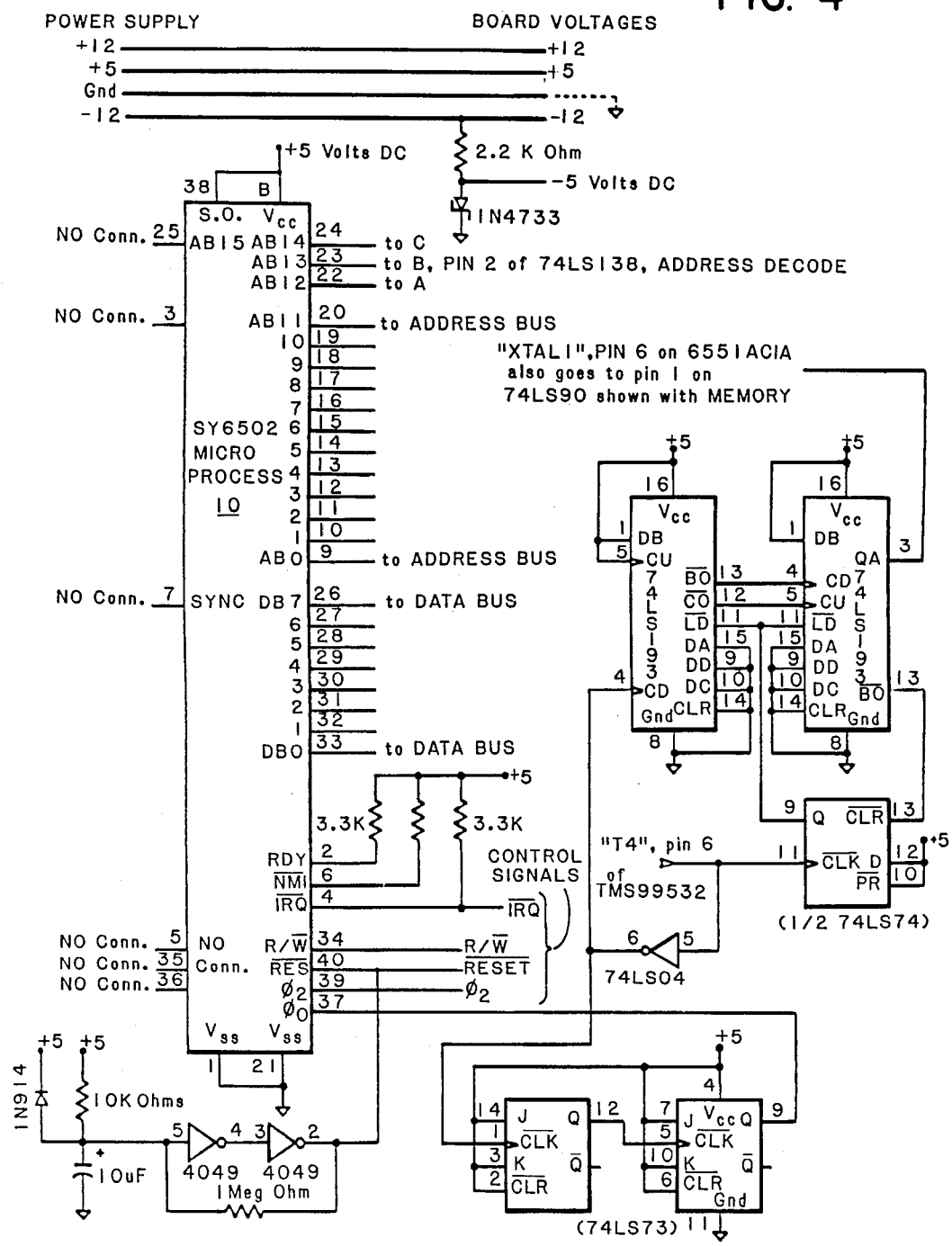
FIG. 4 is a schematic diagram of a preferred microprocessor, reset and time base system used in the telemanometer of FIG. 3.
Figure 5:
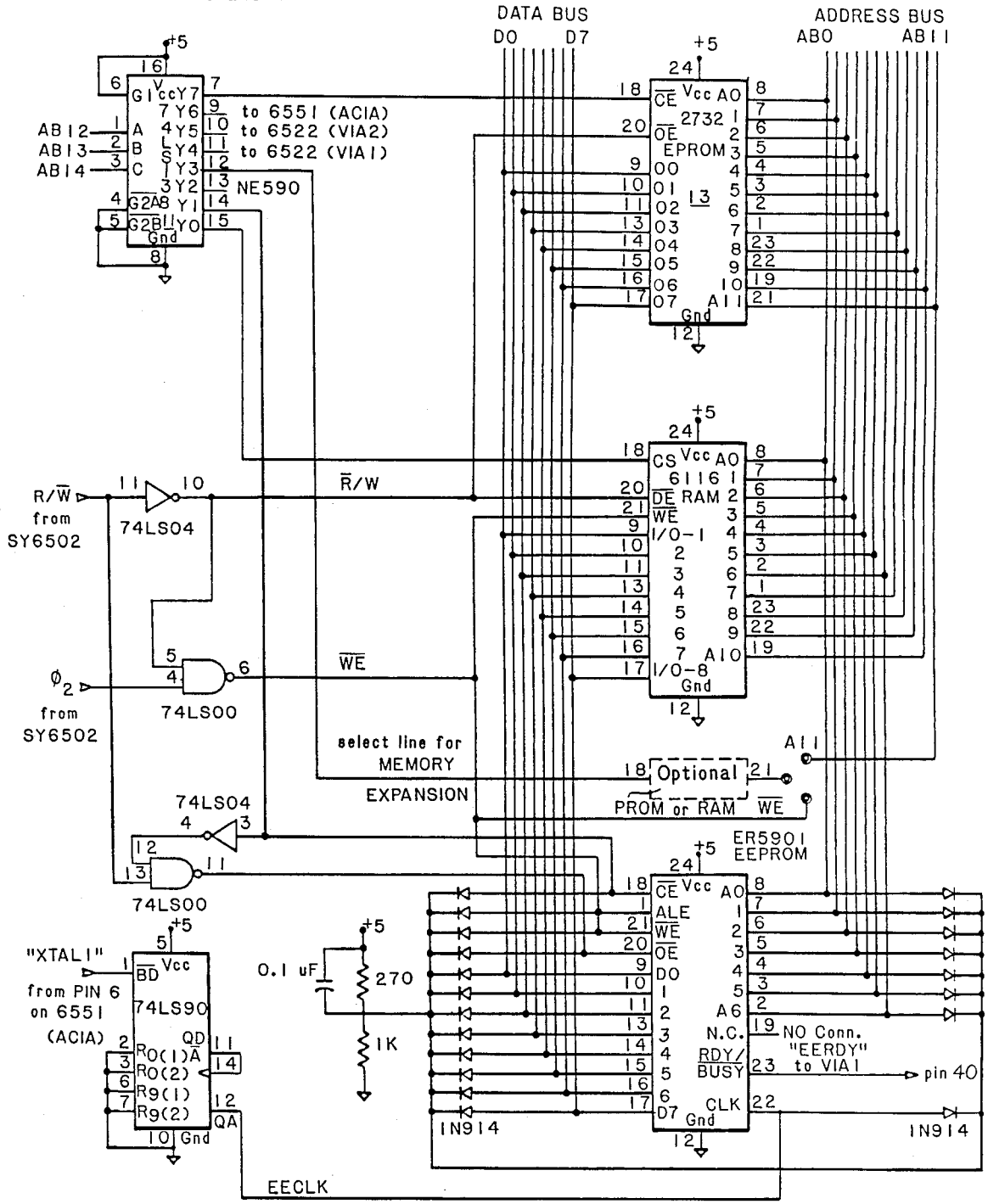
FIG. 5 is a schematic diagram of a preferred memory chip and address decode system used in the telemanometer of FIG. 3.
Figure 6:
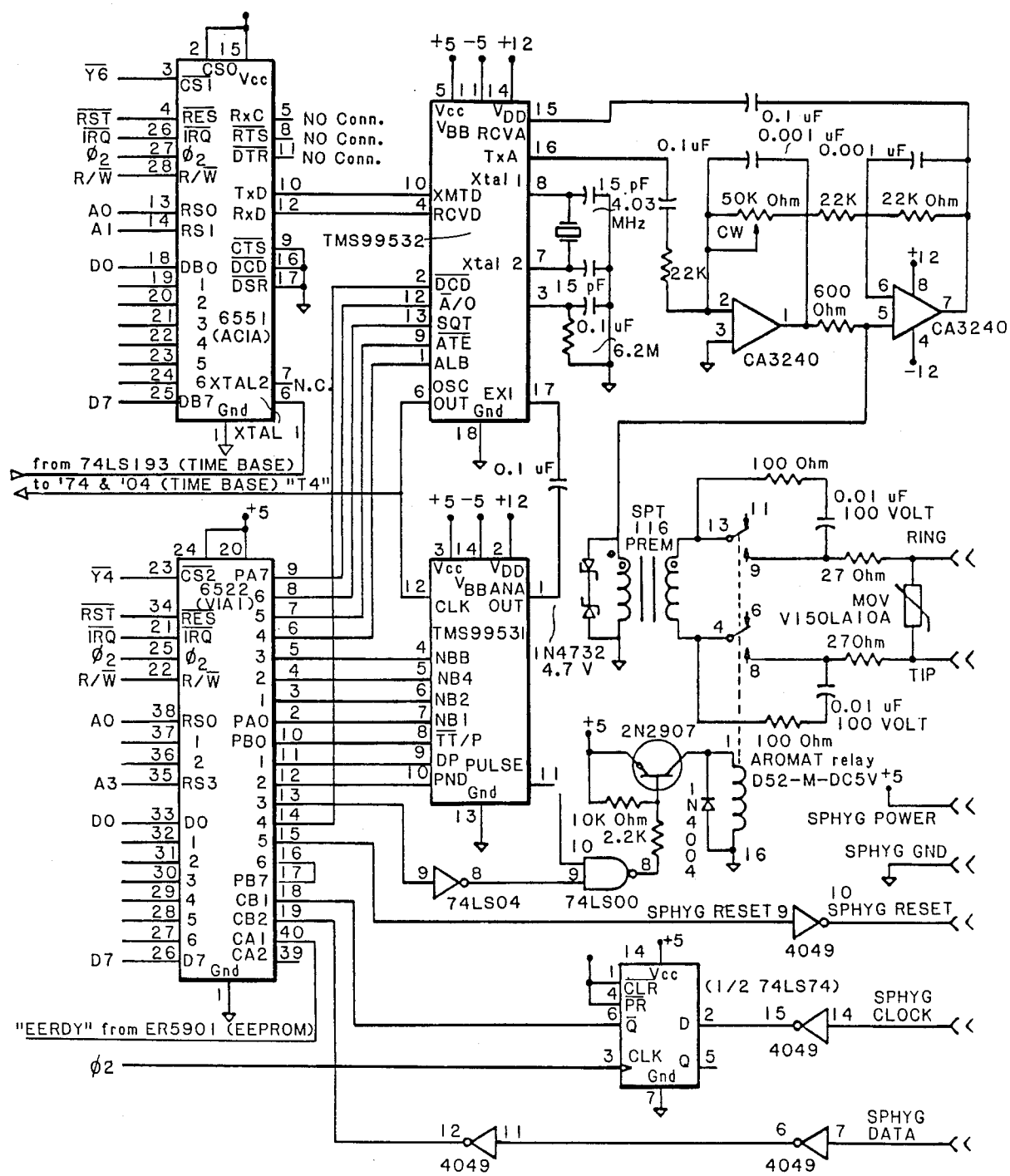
FIG. 6 is a schematic diagram of modem and SPHYG interface system used in the telemanometer of FIG. 3.

A modification of the method of the present invention is also illllustrated in the block diagram of FIG. 2. The patient is provided with a device with which the patient is trained to take blood pressure. The device includes apparatus which generates a signal representing the patient's blood pressure and heart rate readings. The device also includes an electronic data storage medium for storing the generated signals in a form suitable for transmission by means of existing telephonic communication systems. A remote central digital processor includes apparatus for addressing the patient's electronic data storage medium according to a predetermined schedule to access the stored signals representing the patient's blood pressure and heart rate readings. Utilizing such a system, a series of vital signs readings could be taken over a predetermined period of time and stored in the data storage medium located, for example, in the patient's home. The remote central digital processor which can be located, for example, in a physician's office or other health care institution, would access and interrogate the home storage medium according to an established routine which would include repeated attempts to contact or reinterrogate the home storage medium if the phone line were to be in use during a previously attempted interrogation. Such attempts to reinterrogate the home storage medium would be expected after the expiration of a time period of a predetermined duration.

As previously described, the remote central digital processor is programmed to include a predetermined set of criteria for each patient's blood pressure data. The results of the analysis of the blood pressure reading can alternately be submitted to the patient's physician or the patient himself. In the case of submission to the physician, the physician would be in a position to develop a course of treatment based at least in part on the results of the data analysis. The physician could then specify the particular information to be submitted to the patient.

In addition to the periodic interrogation of the patient's home data storage medium by the central digital processor as described above, the present method can incorporate an additional step. The central digital processor can include, in combination with the home apparatus, apparatus for notifying the patient that a scheduled blood pressure reading should be made, or that one or more scheduled readings has been missed.

In FIGS. 3 through 6 there is illustrated in schematic form a preferred embodiment of telemanometer for use in this invention. In these figures, there is illustrated a general purpose 8 bit microcomputer 10 which performs all of the arithmetic and logic operations necessary to control a remote sphygmanometer. Decoder 11 decodes address bits AB12, AB13 and AB14 of microcomputer 10 to provide unique select lines for all the RAM, ROM and 1/0 devices on the printed circuit board.

Reset circuitry 12 provides an automatic "power on" reset function for the processor 10 and 1/0 devices. The RES line is held low for a fixed time period immediately following application of power to the printed circuit board.

An Ultra Violet "Erasable/Programmable Read Only Memory" (EPROM) 13 provides 4,096×8 bits of read only memory which contains all the program instructions required by the microprocessor 10. The EPROM 13 is factory programmed and cannot be field altered. The memory of the EPROM 13 is "non-volatile" and will not be erased when power is removed from the printed circuit board.

A random access memory (RAM) 14 having 2,048×8 bits of memory is connected to a data bus 15 and an address bus 16 along with EPRAM 13. This RAM provides temporary storage for variables and data needed by the microprocessor 10. The contents of this memory will be lost if power is removed from the printed circuit board.

EEPROM 17 is connected to data bus 15 and address bus 16 and provides 128×8 bits of non-volatile random access memory. Data written into EEPROM 17 will survive even if power is removed from the microprocessor circuit board. The EEPROM 17 is used to store "user specific" data that cannot be lost if power is removed from the board.

Time base circuitry (FIG. 4) is provided which generates several highly accurate clock frequencies using a 4.032 MHz crystal as a time base. A 1/0 clock in the microcomputer 10, an XTAL1 clock in an Asynchronous Communications Interface Adapter (ACIA) 18, and a program clock in the EEPROM 17 are all derived by dividing the 4.032 MHz clock rate by fixed constants.

The Asynchronous Communications Interface Adapter 18 provides standard ASC II Serial to Parallel and Parallel to Serial Conversion for the microcomputer 10. All functions of the ACIA 18 are fully controlled by microcomputer 10.

A complete Bell 201 modem interface 19 allows standard ASC II transmission over ordinary customer telephone lines. Fully bidirectional (Full Duplex) communication is provided using two frequencies for transmission and two for reception.

A programmable dialer interface 20 provides both pulse and touch tone (DTMF) dialing capabilities as a companion to the modem 19 and shares related circuitry with the modem.

A duplexer circuit 21 provides transmit gain control, telephone line impedance matching and transmit signal nulling functions.

Transformer 22 provides the necessary isolation between the printed circuit board electronics and the user's telephone line.

An Aromat DS2-M-DC5V relay 23 provides an electronically isolated means of connecting and disconnecting the modem and dialing electronics from the user telephone line. If pulse dialing is selected, this relay is opened and closed under the control of dialer 20 to dial a telephone number.

A general purpose input/output port 24 is used to buffer output and input signals needed by the microcomputer 10. In addition, two internal programmable timers are used as an accurate time base for software controlled timing functions. An on chip shift register is also used in this post to receive serial data from the sphygmanometer microcomputer 10.

A second general purpose input/output port 25 is used to buffer user selected switch inputs.

Figure 7:
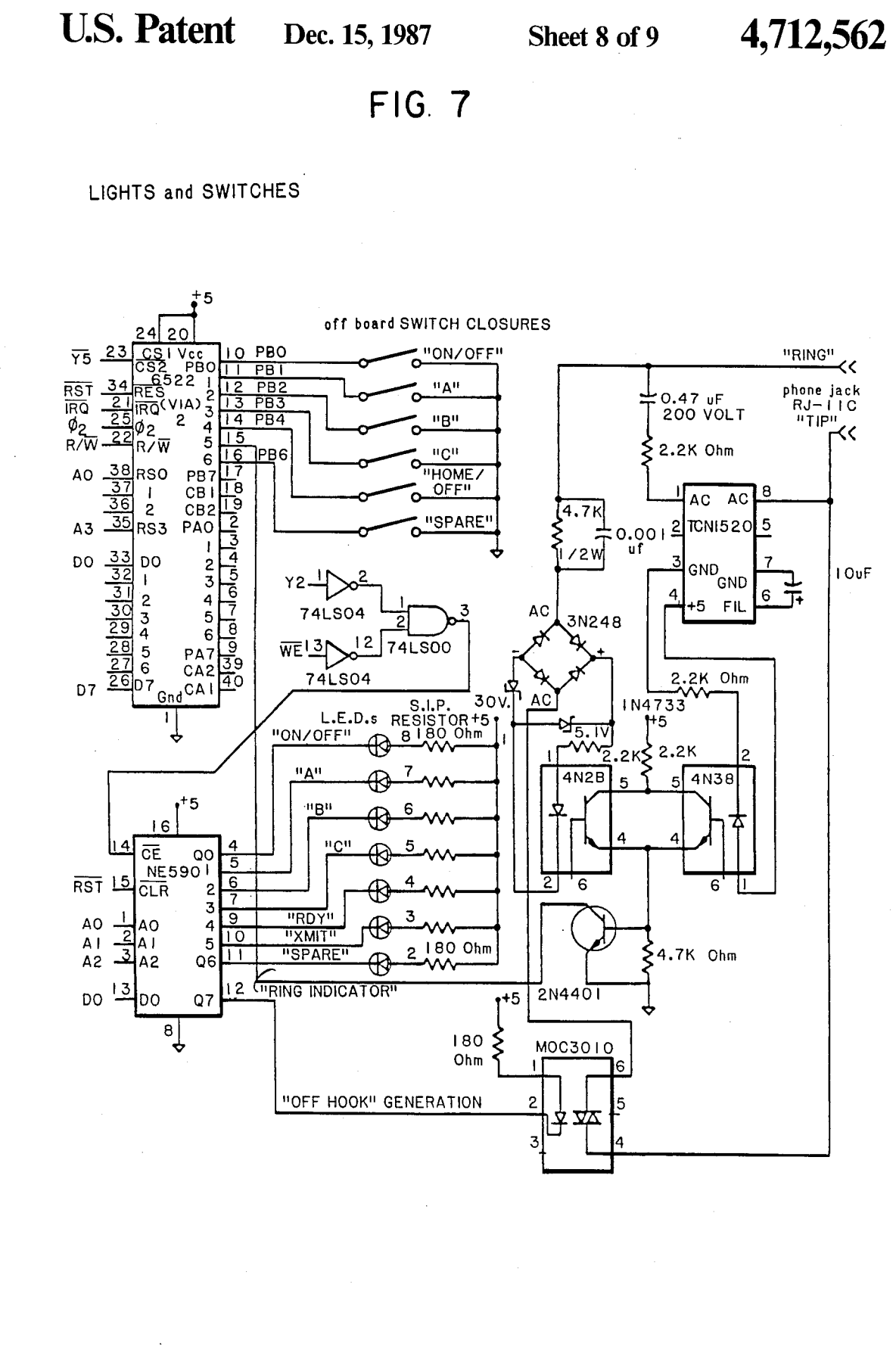

A buffer LED driver chip 26 allows the microcomputer 10 to turn on and off the indicator lamps (LED) (FIG. 7) used to show the system status.

An off hook and ring detect circuit 27 generates an "off hook" condition to obtain a dial tone from a local phone office. Dialing can thereafter be carried out. This circuitry also checks to see if the phone line is already in use before attempting to dial out. This circuit is particularly set out in FIG. 8 and forms an important part of the invention.

The purpose of the off hook and ring detect circuit 27 is to determine whether any other telephone device connected to this trunk line is currently off hook. If another device on the line is already "off hook", then the telemanometer will not attempt to go off hook. This prevents the telemanometer from interfering with an ongoing telephone conversation or other use of the phone line.

The off-hook detect circuit is directly connected to the incoming trunk line's "ring" and "tip" circuits. For safety reasons, and to comply with FCC Regulations, the "ring" and "tip" lines must be electrically isolated from the low voltage circuitry associated with the microprocessor. The required 1500 VOLT isolation is provided by the optocoupler 28 and the optically coupled triac 29. These optically coupled devices provide sufficient isolation to prevent lightening-strikes or accidental shorting of the phone lines and power lines from creating a danger to anyone using the telemanometer.

"Off-Hook" detection is accomplished by measuring the absolute voltage present across the incoming "ring" and "tip" lines. If no other device is currently "off-hook" on this circuit, then the central office battery voltage will appear across the "ring" and "tip" lines. The central office battery voltage is nominally 48 Volts DC. The polarity of this voltage is supposed to be guaranteed. However, faulty interior telephone wiring will often cause the "ring" and "tip" lines to be reversed. Therefore, this circuitry was designed to operate with any battery polarity. Detection of the central office battery voltage indicates that the phone line is not currently occupied. If another telephone device is currently "off-hook" on the same trunk line then the voltage across the "ring" and "tip" will drop to below 10 Volts DC. Detection of this lower voltage indicates that the phone line is currently occupied. The circuit which detects this voltage difference is decribed below.

For the first case, assume that no devices, including the telemanometer, are "off-hook". Thus a DC Voltage of approximately 48 Volts and unknown polarity exists across the "ring" 30 and "tip" 31 lines.

Before activation, our circuitry presents a very high impedance to the phone lines. This high impedance is insured by the de-energized triac output of the optically isolated triac 29 labeled "0.C.T.1". Thus, until activation, our detection circuitry will in no way interfere with the normal operation of the phone lines.

To activate the "off-hook" detect circuit, pin 2 of triac 29 (0.C.T.1) is driven to near ground potential by an external circuit i.e. drive 26 (NE590) controlled by the microprocessor chip 10. This allows sufficient current, determined by resistance 32, also labeled "R5", to flow through the Light Emitting Diode to activate the triac output of 0.C.T.1. The "tip" line will therefore be electrically connected to the lower AC input connection of the diode bridge 33 labeled "DB1". The "ring" line is connected to the top AC inpu of DB1 by resistance 34 (R1) and condenser 35 (C1). Resistance 34 (R1) serves to limit the current taken from the phone lines to approximately 2 mA. This small current will not significantly affect the voltage across the "ring" and "tip" lines. Diode bridge 33 (DB1) insures that the current flow through the rest of the detection circuitry is of known polarity regardless of the polarity of the incoming voltage. The current flowing from the 30 (positive) terminal of DB1 is split between the Zener Diode 36 (Z2) and the resistor 37 (R2). The current through R2 is limited to approximately 1.8 mA by the voltage clamping action of Zener Diode 36. Thus, approximately 0.2 mA of the available 2.0 mA of current flows through Z2. The 1.8 mA flowing through R2 also flows through the Light emitting input diode of the optical coupler 28 labeled "0.C.1". This current and the remaining current from Z2 flow back through Zener Diode 38 (Z1), through the −(negative) input of DBl, and subsequently back into the telephone lines. The approximately 35 Volt drop across Zener Diodes Z1 and Z2 insure that this circuit will not conduct current unless at least 35 Volts appears across the "ring" and "tip" lines. In this case, sufficient current will be provided by the 48 Volt central office battery to activate the Light Emitting Diode in 0.C.1. The resulting photons will excite the output transistor of 0.C.1. Current will thus flow from the +5 Volt power supply through resistor 39 (R3), through the output transistor of 0.C.1, and into resistor 40 (R4) and the Base of transistor 41 (Q1). This current is sufficient to saturate transistor Q1 and to drive it's collector to near ground potential. The saturation of Q1 is used to indicate that the full 48 Volt battery voltage is present across the "ring" and "tip" lines.

In the second case, some other device is "off-hook" and the voltage across "ring" and "tip" is less than 10 volts. Here, the activation of 0.C.T.1 brings only 10 Volts across the AC inputs of DB1. The resulting output voltage across the +and −pins of DB1 is insufficient to activate Zener Diode Z1. Thus, no current may flow through Zener Diode Z2 or the Light Emitting Diode input of 0.C.1. With no current input to 0.C.1 there will be no current flow through the output transistor of 0.C.1. The emitter-base voltage of Q1 will fall to 0 (zero) Volts and Q1 will turn off. When transistor Q1 is off, it indicates (through a line to VIA2) that some other device is "off-hook" on this circuit.

What has been described above is a method for the continuous treatment and diagnosis of cardiovascular disorders as well as a method for the monitoring of a prescribed treatment of medication for a patient with immediate feedback provided with analysis to the patient and his physician.

The foregoing specification sets out certain preferred practices and embodiments of this invention, however it will be understood that this invention may be otherwise embodied within the scope of the following claims.

We claim:

1. A system for providing information pertaining to a blood pressure of a patient utilizing telephone lines, including a ring line and a tip line, said system comprising:

means for generating signals representing the level of blood pressure of a patient and signals representing the identity of to which patient, of at least two patients, the blood pressure signals pertain, said signals being suitable for transmission over said telephone lines;

a remote central digital processor; and means for transmitting said blood pressure signals and said patient identifying signals over said telephone lines to said remote central digital processor, and including an off hook detecting circuit having voltage measuring means for measuring voltage across said ring and tip lines, and switching means responsive to the measured voltage and operative to connect said transmitting means to the telephone lines only when said voltage is above a predetermined voltage indicating that the telephone lines are not in use, said central processor including storage means which stores said blood pressure signals in a form suitable for latter access, and analyzing means which analyzes said blood pressure signals according to predetermined criteria.

2. The system of claim 1 wherein said voltage measuring means includes a diode bridge circuit, connecting means for selectively connecting the A-C inputs of the diode bridge across the ring and tip lines, and a voltage divider connected across the output terminals of said diode bridge and comprising a zener diode in series with a resistor, and wherein said switching means includes a light emitting diode in series with said resistor and zener diode, said light emitting diode being turned on only when the voltage across said ring and tip line is above said predetermined voltage, a photo transistor which is turned on by photons emitted by said light emitting diode when the light emitting diode is turned on, and a saturable transistor which is driven into saturation when said photo transistor is turned on, saturation of said saturable transistor providing the indication that the telephone lines are not in use.

3. The system of claim 1 wherein said analyzing means includes means for determining the sufficiency of said signals representing the level of blood pressure of the patient, and means for sending over the telephone lines back to said means for generating said blood pressure signals, a feedback signal calling for an additional blood pressure reading when said signals representing the level of blood pressure are insufficient, and wherein said means for generating said blood pressure signals includes means responsive to the feedback signal for generating an indication of a need for an additional blood pressure reading.

* * * * *